United States Patent [19]

Blaine

[11] Patent Number: 4,817,626

[45] Date of Patent: Apr. 4, 1989

[54] NASAL EXHALER AND METHOD

[76] Inventor: Hal Blaine, P.O. Box 6166, Phoenix, Ariz. 85261

[21] Appl. No.: 219,881

[22] Filed: Jul. 11, 1988

Related U.S. Application Data

[63] Continuation of Ser. No. 042,681, Apr. 27, 1987, abandoned.

[51] Int. Cl.4 ............................................. A61B 5/08
[52] U.S. Cl. ............................ 128/728; 128/205.13; 604/212
[58] Field of Search ................... 128/716, 727–728, 128/205.13–205.14; 604/212–216

[56] References Cited

U.S. PATENT DOCUMENTS

| | | | |
|---|---|---|---|
| 1,261,608 | 4/1918 | Peterson | 604/212 |
| 1,481,008 | 1/1924 | Hodlick | 604/212 |
| 1,507,475 | 9/1924 | Flagg | 604/212 |
| 1,734,426 | 11/1929 | Graham | 604/212 |
| 2,492,326 | 12/1949 | Scotti | 604/212 |
| 2,516,762 | 7/1950 | Dwyer | 128/205.13 |
| 2,823,667 | 2/1958 | Raiche | 128/205.13 |
| 3,070,089 | 12/1962 | Dick | 128/205.13 X |
| 3,333,844 | 8/1967 | Jurschak | 128/728 X |
| 3,502,078 | 3/1970 | Hill et al. | 604/212 |
| 3,895,533 | 7/1975 | Steier | 128/727 X |

Primary Examiner—Kyle L. Howell
Assistant Examiner—Angela D. Sykes
Attorney, Agent, or Firm—Harry M. Weiss

[57] ABSTRACT

A nasal exhaler is disclosed which simply and efficiently allows for equalization of atmospheric pressure within eustachian tubes, sinus cavitites, and ear drums. The disposable exhaler includes a hollow member detachably coupled with a balloon-type inflatable bag. The hollow member is positioned over the opening of one nostril and the user exhales into the hollow member while holding the remaining nostril closed. After the process has been performed on both nostrils the passages are cleared.

7 Claims, 1 Drawing Sheet

U.S. Patent     Apr. 4, 1989     4,817,626
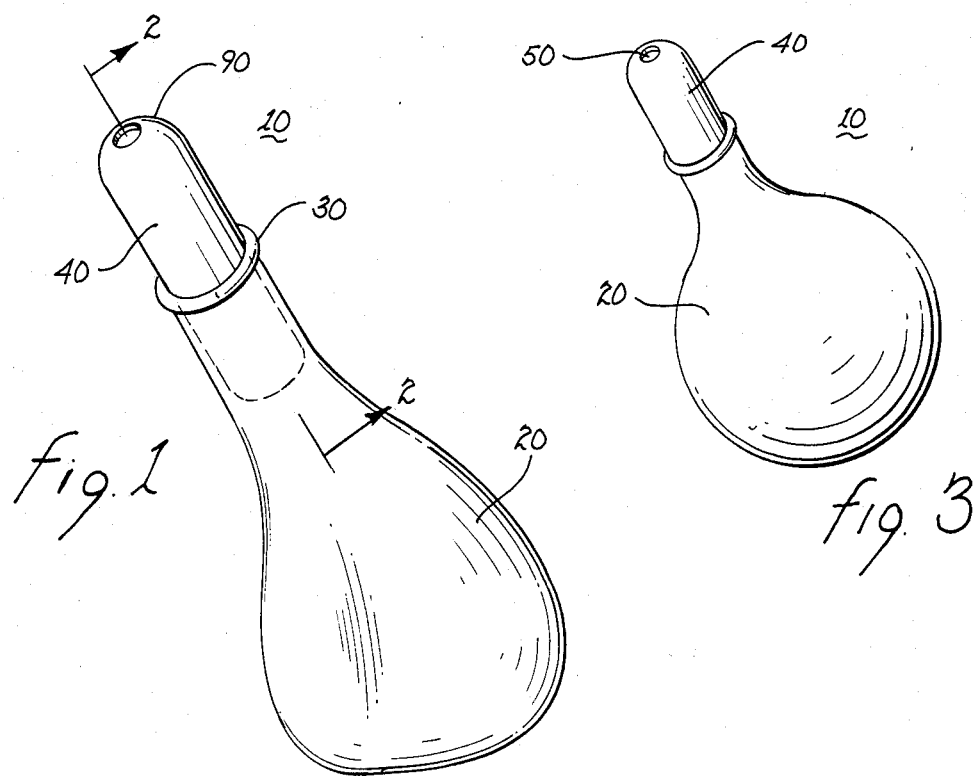
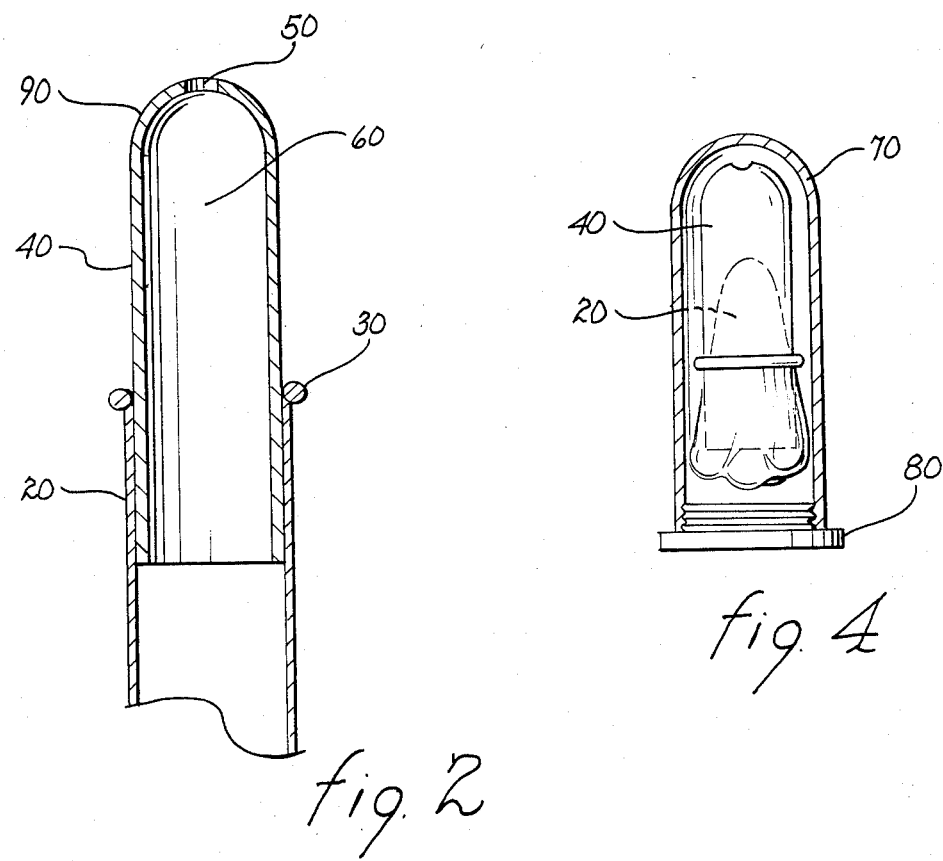

NASAL EXHALER AND METHOD

This is a continuation of co-pending application Ser. No. 042,681, filed on Apr. 27, 1987, now abandoned.

BACKGROUND OF THE INVENTION

1. Field of the Invention

The present invention generally relates to a nasal exhaler and, more specifically, to a nasal exhaler for manually facilitating the clearance of eustachian tubes and sinus cavities especially for use when a person is subject to relatively quick increases in atmospheric pressure such as occurs during aviation.

2. Description of the Prior Art

In the past, a tool for facilitating the manual clearance of eustachian tubes was not available for general public use. A person was limited to a few methods of clearance, all of which have distinct drawbacks.

A first series of aidless methods includes purposeful swallowing, yawning, or chewing gum to open the eustachian tubes and thereby equalize the atmospheric pressure on either side of the ear drum. This series of methods, although relatively safe, are generally ineffectual when the eustachian tubes are even the slightest congested.

A second series of aidless methods includes the action of closing the nostrils and mouth while applying exhalent pressure to increase the atmospheric pressure within the eustachian tube and thereby forcing the ear drum to "pop". This second series of methods is more effective than the first series, yet is significantly more dangerous because the exhalent pressure is applied without adequate control facilities which condition may lead to a sudden and powerful increase in pressure within the eustachian tube and inner ear, especially if congestion is present. Thus, the ear drum is subjected to a high level of unreleased pressure from the inside and may rupture resulting in serious injury.

Another series of methods utilizes chemical or pharmaceutical reactants. The employment of these reactants inherently includes subjecting the user to unnatural physical conditions, negative side effects, delayed chemical reactions, and more than minimal money costs.

The prior art reveals several examples of respiratory devices. for example, Etzlinger (U.S. Pat. No. 3,303,840) discloses an apparatus for collecting and analyzing alveolar gas from the lungs. Watson et al. (U.S. Pat. No. 4,327,741) disclose a device for measuring respiration volume. A spirometer device is taught by Petty et al. (U.S. Pat. No. 4,291,704) for measuring lung capacity. A breathing exerciser, for developing a stronger respiratory system in persons suffering from certain maladies of the bronchi and lungs, presented by Navara (U.S. Pat. No. 3,949,984). Bolton et al. (U.S. Pat. No. 4,579,826) provide a method and device for analyzing human breath and for amusement. All of the above-cited references (Etzlinger, Watson et al., Petty et al., Navara, and Bolton et al.) disclose a device activated when in contact with a person's mouth. Dali (U.S. Pat. No. 4,367,735) presents a nasal cannula to be connected between the nostrils of a medical patient and a hose leading to a respirator or other respiration assistance device.

None of above-identified references disclose a nasal exhaler for clearing eustachian tubes and sinus cavities.

Accordingly, there is a distinct need to provide device which eliminates the aforementioned flaws in the art.

SUMMARY OF THE INVENTION

It is an object of this invention to provide a nasal exhaler.

It is a further object of this invention to provide a nasal exhaler to aid in the clearing of eustachian tubes and sinus cavities.

It is a further object of this invention to provide a nasal exhaler which may be employed with safety.

It is a further object of this invention to provide a nasal exhaler which is simple in construction, convenient in use, and relatively inexpensive to manufacture.

It is a still further object of this invention to provide a nasal exhaler which is disposable.

The foregoing and other objects, features and advantages of this invention will be apparent from the following, more particular, description of the preferred embodiments of this invention, as illustrated in the accompanying drawings.

BRIEF DESCRIPTION OF THE DRAWINGS

FIG. 1 is a perspective view of the nasal exhaler.

FIG. 2 is a cross sectional view taken along the line 2—2 of FIG. 1 in the direction of the arrows.

FIG. 3 is a perspective view of the nasal exhaler in expanded mode.

FIG. 4 is a cross sectional view of the nasal exhaler inside one embodiment of a package device.

DESCRIPTION OF THE PREFERRED EMBODIMENT

As seen in FIG. 1, of the accompanying drawings which set forth the present invention in greater detail and in which like numerals designate like elements, the nasal exhaler is generally illustrated comprising a balloon-type resiliently inflatable bag 20, a rim portion 30 of the bag 20, and a hollow member 40.

The inflatable bag 20 overlaps and is frictionally coupled with a lower portion of the hollow member 40. The hollow member 40 may be constructed of molded or injected plastic. The inflatable bag 20 may be replaceable and may be attached or detached with ease. Near the upper end of the hollow member 40, the circumference thereof decreases to form a dome-shaped structure 90. An orifice 50 is located in the top portion of said dome-shaped structure 90.

As seen best in FIG. 2, the orifice 50 provides a port through which air may move through an air passage 60 into and out of the inflatable bag 20.

Referring to FIG. 3, the nonporous and resiliently inflatable bag 20 is illustrated in an expanded mode indicating a higher level of atmospheric pressure within the bag 20 than on the outside thereof.

Referring now to FIG. 4, one embodiment of the nasal exhaler is shown. This embodiment includes a case for surrounding and packaging the nasal exhaler. The case is constructed of plastic and consists of two parts. The first part consists of a hollow upper portion 70 which is of a similar yet larger shape compared to the hollow member 40. Unlike the hollow member 40, the hollow portion 70 does not contain an orifice. The second part consists of an inverted cap 80 of slightly larger diameter than the hollow portion 70. The hollow portion 70 and the cap 80 are cooperatively threaded and thus are detachable coupled to form a complete casing around the exhaler 10. When encased for storage the nasal exhaler 10 is manipulated so that the majority of the inflatable bag 20 is positioned within the air passage 60 area of the hollow member 40.

SYSTEM OPERATION

The method of operation and use for the nasal exhaler 10 is as follows. The exhaler 10 is removed from the casing after the hollow portion thereof 70 has been detached from the cap portion thereof 80.

The dome-shaped portion 90 of the tubular member 40 is positioned at the opening of one nostril so that a relatively air tight seal is formed therebetween. The eustachian tubes and sinus cavities are cleared when the remaining nostril is closed while the user exhales through the orifice 50 and the air passage 60 causing the inflatable bag 20 to exit the hollow member 40 and expand (as shown in FIG. 3). This same process is then repeated from the remaining nostril.

The resilient and expandable characteristics of the inflatable bag 20 significantly reduce the danger of ear drum rupture associated with some conventional methods of clearing.

While the invention has been particularly shown and described in reference to the preferred embodiments thereof, it will be understood by those skilled in the art that changes in form and details may be made without departing from the spirit and scope of the invention.

I claim:

1. A method for equalizing atmospheric pressure on opposite sides of an ear drum comprising the steps of:
   inhaling air;
   providing a nasal exhaler having a resiliently inflatable bag;
   providing a hollow member with openings on each end thereof, said hollow member being frictionally, operably, and detachably, coupled with said inflatable bag at a first end thereof, said coupling being air-tight; said hollow member having external surface means having a configuration for providing an air-tight seal adjacent a second end portion thereof with a rim portion of a person's nostril; and said hollow member having means for allowing the flow of air therethrough the openings on each end thereof; and thereafter
   inflating said bag by forcibly exhaling through a first nostril of a pair of nostrils into said hollow member while blocking a second nostril of said pair of nostrils to cause the eustachian tubes air pressure to become equalized and to prevent the possibility of rupturing an eardrum.

2. A method in accordance with claim 1 further comprising the steps of:
   providing a dome-shaped portion of said hollow member located at said second end thereof, said resiliently inflatable bag being operably coupled to said first end of said hollow member; and
   providing an orifice passing through an apex of said dome-shaped portion.

3. A method in accordance with claim 2 wherein said inflatable bag comprises:
   a body portion; and
   a neck portion, said neck portion being coupled with said first end of said hollow member.

4. A method in accordance with claim 3 wherein said inflatable bag comprises a balloon.

5. A method in accordance with claim 4 wherein said neck portion of said inflatable bag has a diameter to fit snugly over said first end of said hollow member, said neck portion of said inflatable bag has a rim circumferentially positioned at an open end thereof, said body portion of said inflatable bag is generally spherical in shape, said hollow member is tubular in shape, said dome-shaped portion of said hollow member has a diameter to permit a generally air-tight seal with a nostril, and said hollow member has an aperture running therethrough along a center longitudinal axis thereof.

6. A method in accordance with claim 2 wherein said hollow member is constructed of plastic.

7. A method in accordance with claim 1 further providing:
   a case means for enclosing said resiliently inflatable bag and said hollow member, said case means comprising a base portion and a tubular portion having threads for cooperatively, and detachably, engaging and disengaging said base portion.

* * * * *